US009810686B1

(12) United States Patent
Hall et al.

(10) Patent No.: US 9,810,686 B1
(45) Date of Patent: Nov. 7, 2017

(54) URINALYSIS CASSETTE AND SYSTEM

(71) Applicants: David R. Hall, Provo, UT (US); Dan Allen, Springville, UT (US); Joshua Larsen, Spanish Fork, UT (US); Ben Swenson, Lehi, UT (US); Jared Reynolds, Pleasant Grove, UT (US); Joe Fox, Spanish Fork, UT (US); Lloyd J. Wilson, Herriman, UT (US)

(72) Inventors: David R. Hall, Provo, UT (US); Dan Allen, Springville, UT (US); Joshua Larsen, Spanish Fork, UT (US); Ben Swenson, Lehi, UT (US); Jared Reynolds, Pleasant Grove, UT (US); Joe Fox, Spanish Fork, UT (US); Lloyd J. Wilson, Herriman, UT (US)

( * ) Notice: Subject to any disclaimer, the term of this patent is extended or adjusted under 35 U.S.C. 154(b) by 0 days.

(21) Appl. No.: 15/265,144

(22) Filed: Sep. 14, 2016

(51) Int. Cl.
G01N 21/00 (2006.01)
G01N 33/52 (2006.01)
A61B 5/20 (2006.01)
A61B 5/00 (2006.01)
A61B 10/00 (2006.01)

(52) U.S. Cl.
CPC ........... *G01N 33/521* (2013.01); *A61B 5/207* (2013.01); *A61B 5/742* (2013.01); *A61B 10/007* (2013.01)

(58) Field of Classification Search
USPC ...................................................... 422/82.05
See application file for complete search history.

(56) References Cited

U.S. PATENT DOCUMENTS

| 4,943,416 | A | * | 7/1990 | Kikuchi | G01N 35/00029 422/63 |
| 4,961,431 | A | * | 10/1990 | Ikenaga | A61B 5/20 600/573 |
| 5,111,539 | A | * | 5/1992 | Hiruta | A61B 5/02241 4/301 |
| 6,081,935 | A | * | 7/2000 | Kishi | E03D 7/00 4/213 |
| 2006/0229531 | A1 | * | 10/2006 | Goldberger | A61B 5/145 600/573 |

(Continued)

*Primary Examiner* — Jill Warden
*Assistant Examiner* — Brittany Fisher

(57) ABSTRACT

A urinalysis cassette and system that includes a toilet, into which a urinalysis cassette is inserted. The cassette is comprised of a roll of color-change-reagent strips. Each strip includes a plurality of strip sections wherein an absorbent material is imbued with color-change reagent, or onto which one or more color-change reagents are dispensed. The color-change-reagent strips are consecutive and contiguous on the roll. A cassette includes two spools arranged such that when the spools turn, the reagent strip moves from a first (source spool) to a second (waste spool). The section of the reagent strip that is between the two spools may be exposed to a urine specimen. The absorbent-material strips that have been exposed to both a urine specimen and a color-change reagent may undergo a chemical reaction. Selective-lighting illumination may be applied to absorbent-material strips that have undergone such chemical reactions to measure reflectivity of certain color wavelengths. This measurement may be expressed in terms of a digital readout, which may be displayed on a user interface.

19 Claims, 14 Drawing Sheets

(56) References Cited

U.S. PATENT DOCUMENTS

| | | | |
|---|---|---|---|
| 2007/0119710 A1* | 5/2007 | Goldberger | G01N 33/48764 204/403.01 |
| 2007/0273868 A1* | 11/2007 | Yano | B01J 47/04 356/36 |
| 2007/0276270 A1* | 11/2007 | Tran | A61B 5/0022 600/508 |
| 2009/0215159 A1* | 8/2009 | Kirby | A61B 10/0096 435/287.2 |
| 2015/0283824 A1* | 10/2015 | Aihara | B41J 2/325 400/225 |

* cited by examiner

US 9,810,686 B1

URINALYSIS CASSETTE AND SYSTEM

CROSS-REFERENCE TO RELATED APPLICATIONS

This application claims the benefit of U.S. Provisional Application No. 62/303,329 filed Mar. 3, 2016, the contents of the application being incorporated herein by reference.

TECHNICAL FIELD

The present disclosure relates generally to the field of urinalysis. More specifically, the present disclosure relates to an improved instrument for urinalysis.

BACKGROUND

Medical professionals often utilize urine as a source of information to diagnose, monitor, and/or assess the health conditions of an individual. Urine can be an important source of information for various dysfunctions such as pancreatic disorders (typically, diabetes), liver disease, kidney disorders, and a variety of other health related conditions. Conventional urinalysis includes a dipstick that often must be tested with a device that is different and separate from the toilet apparatus upon which a person may sit when providing the urine sample. Additionally, the processes of providing a urine sample can be cumbersome, uncomfortable, and intrusive. Embodiments disclosed herein provide improvements to the urinalysis equipment involved in sampling urine so as to assist individuals in rendering a health check.

SUMMARY OF THE INVENTION

Disclosed herein is a toilet, comprising a urinalysis cassette and system, which may overcome the limitations of existing urinalysis methods and systems. In one embodiment, a toilet comprises a urinalysis cassette wherein a roll of contiguous strips extends from a first spool to a second spool. A portion of the roll of contiguous strips, in one embodiment, may traverse a gap between the first and second spool, which is exposed to urine during a urinary event. The exposed portion of the roll of contiguous strips may change between urinary events by winding about the second spool and vacating the first spool, according to one embodiment. The roll of contiguous strips comprises a plurality of absorbent material segments upon which a color-change reagent may come into contact with a urine specimen, according to one embodiment, and induce a chemical reaction. In one embodiment, the chemical reaction may be analyzed using selective-lighting illumination, which may produce a digital readout of the chemical interaction between the urine and the color-change reagent. The digital readout may then be displayed on a user interface.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DESCRIPTION

Figure 1:
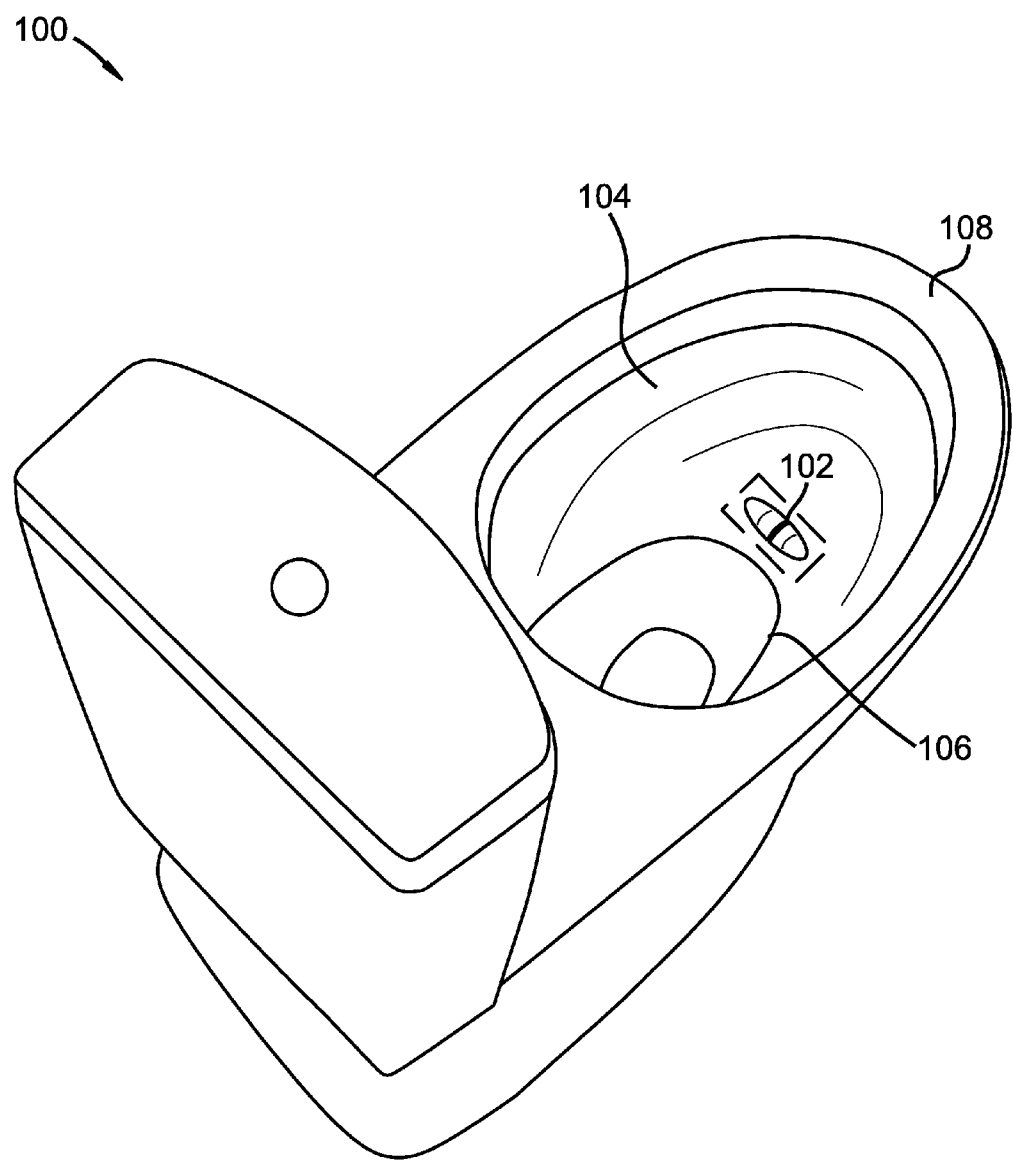
FIG. 1 is a perspective view of a toilet, according to one embodiment, including a urine-specimen-capture slit and a toilet bowl.

The term "toilet," as used herein, may be understood to describe any sanitation fixture designed to receive urine and/or other excreta including a urinal, latrine, lavatory, commode, etc. A toilet is dynamically useful for obtaining health-related measurements due to its frequency of use, relatively easy accessibility, and privacy afforded to the location. In one embodiment, a toilet may include a cassette, which may be inserted into a compartment or housing located within the toilet. A button, lever, or other input may be utilized to insert and/or remove the cassette from the toilet.

According to various embodiments, insertion of the cassette into the toilet compartment may activate a sensor, which may communicate with a nozzle to dispense urine onto a urinalysis strip upon sensing urine from a urinary event. In another embodiment, insertion of the cassette into the toilet compartment may directly open the nozzle such that urine from a urinary event may be dispensed onto a urinalysis strip.

As described herein, a urinalysis cassette may include a roll of contiguous strips with one or more absorbent-material segments. The word "attached," or the phrase "attached to" may to refer to any suitable connection and/or converging interaction between two or more entities which are in direct contact with each other and/or are separated from each other only by a fastener of any suitable variety (e.g., mounting hardware or an adhesive). The roll of contiguous strips may be pre-wound on a first spool and attached to a second spool for receiving and storing strips distributed from the first spool.

According to various embodiments, the first and second spools of the urinalysis cassette may synchronously rotate a pre-programmed distance and/or number of degrees, such that once urinalysis of an exposed strip segment of the roll of contiguous strips is complete, a new segment of the roll of contiguous strips becomes exposed and traverses a gap between the spools. The synchronization may be coordinated, according to one embodiment, with one or more connecting rods that are attached to both the first spool and the second spool, such that one spool's rotation about an axis directly turns the second spool. In another embodiment, the spools may be coordinated using electrical signals, magnetic interactions, and/or any other suitable turning force.

In one embodiment, urine from a urinary event may enter a urine-specimen-capture slit in a toilet bowl. Upon entering the urine-specimen-capture slit, a urine specimen may pass through one or more nozzles, from which the urine specimen may be instantaneously dispensed onto one or more absorbent-material segments on the roll of contiguous strips. The nozzles may be pre-programmed to move and/or rotate to a plurality of absorbent-material segments, according to one embodiment.

In one embodiment, the color-change reagent may imbue and/or be allocated to one or more absorbent-material segments. The urine specimen may be dispensed from the nozzle onto the color-change-reagent-infused absorbent-material segments. After the urine specimen has been dispensed onto one or more absorbent-material segments, the urine may chemically react with the color-change reagent. In another embodiment, one or more nozzles may dispense color-change reagent to the absorbent-material segments after the urine specimen is dispensed onto the absorbent-material segments.

In one embodiment, the toilet may contain one or more piezoelectric inkjet pumps or similar nonthermal microdispensers for dispensing the color-change reagent. The color-change reagent may be stored, according to one embodiment, in a temperature-controlled chamber prior to being applied to the absorbent-material segments.

In another embodiment, the roll of contiguous strips wound around the first spool of the urinalysis cassette may be exposed to a temperature-control mechanism. The temperature-control mechanism may be dormant, in one embodiment, until activated by the presence of urine in the urine-specimen-capture slit. Upon activation, the temperature-control mechanism may be selectively applied to the roll of contiguous strips, according to one embodiment, such that only the segment exposed to the urine specimen is subject to temperature control. In one embodiment, the temperature-control mechanism is activated to incubate the strip of absorbent-material segments, upon which a urine specimen has been applied, only for a period of time sufficient for the urine specimen and the color-change reagent to complete a desired chemical reaction.

Selective-lighting illumination may be applied to the absorbent-material segments after the urine specimen has chemically interacted with the color-change reagent of the absorbent-material segments. According to one embodiment, selective-lighting illumination may include one or more light emitting diodes, photodiodes, and/or cameras. In one embodiment, a light source may be a broadband source, a tunable-narrowband filter, and/or several narrowband emitters. Measuring reflectivity of specific color wavelengths, according to one embodiment, may produce a digital readout of the results from the chemical reaction between the urine specimen and the color-change reagent. In one embodiment, the digital readout may be transmitted via a conductor and/or wireless technology to be stored as computer storage memory. A user interface may, in one embodiment, convey the urinalysis results via a visual signal and/or representation. According to one embodiment, a digital readout may be compared to one or more previous digital readouts, with the comparison displayed on the user interface. In one embodiment, the user interface may be attached to the toilet. Other embodiments may include a user interface that is detached from the toilet.

A heater and/or fan may, according to one embodiment, be activated to dry the absorbent-material segments after they have undergone the chemical reaction between the urine and color-change reagent. In another embodiment, a desiccant may be dispensed onto the moist absorbent-material segments. According to one embodiment, a sanitation and/or purification system may be activated to sanitize the absorbent-material segments and/or sections of the roll of contiguous strips that were exposed to urine. The sanitation and/or purification may comprise the application of ultra-violet radiation, according to one embodiment.

In one embodiment, the urinalysis cassette may comprise a sensor, optical sensor, and/or indicator to detect when the roll of contiguous strips may be entirely transferred from the first spool to the second spool. According to one embodiment, a digital readout may activate a communications network wherein a signal is generated to activate a motor and/or turn the first and/or second spool in preparation for a future urinary event. A motor may be used, in one embodiment, to turn the first and/or second spool. In one embodiment, an electrical source may activate the motor, one or more nozzles to dispense a urine specimen and/or reagent, a temperature control system, purification system, heater, fan, desiccant dispenser, light source, and/or any other mechanized or electrical apparatus comprised in the urinalysis system.

FIG. 1 is a perspective view of a toilet 100, according to one embodiment, including a urine-specimen-capture slit 102 and a toilet bowl 104. The urine-specimen-capture slit 102 may be positioned in between the water 106 and the front of the toilet-bowl rim 108 such that a user may urinate in a natural standing or sitting position and urine will be dispensed onto the urine-specimen-capture slit 102. The toilet 100 may be comprised of porcelain, ceramic, plastic, glass, metal, and/or any other suitable material.

Figure 2A:
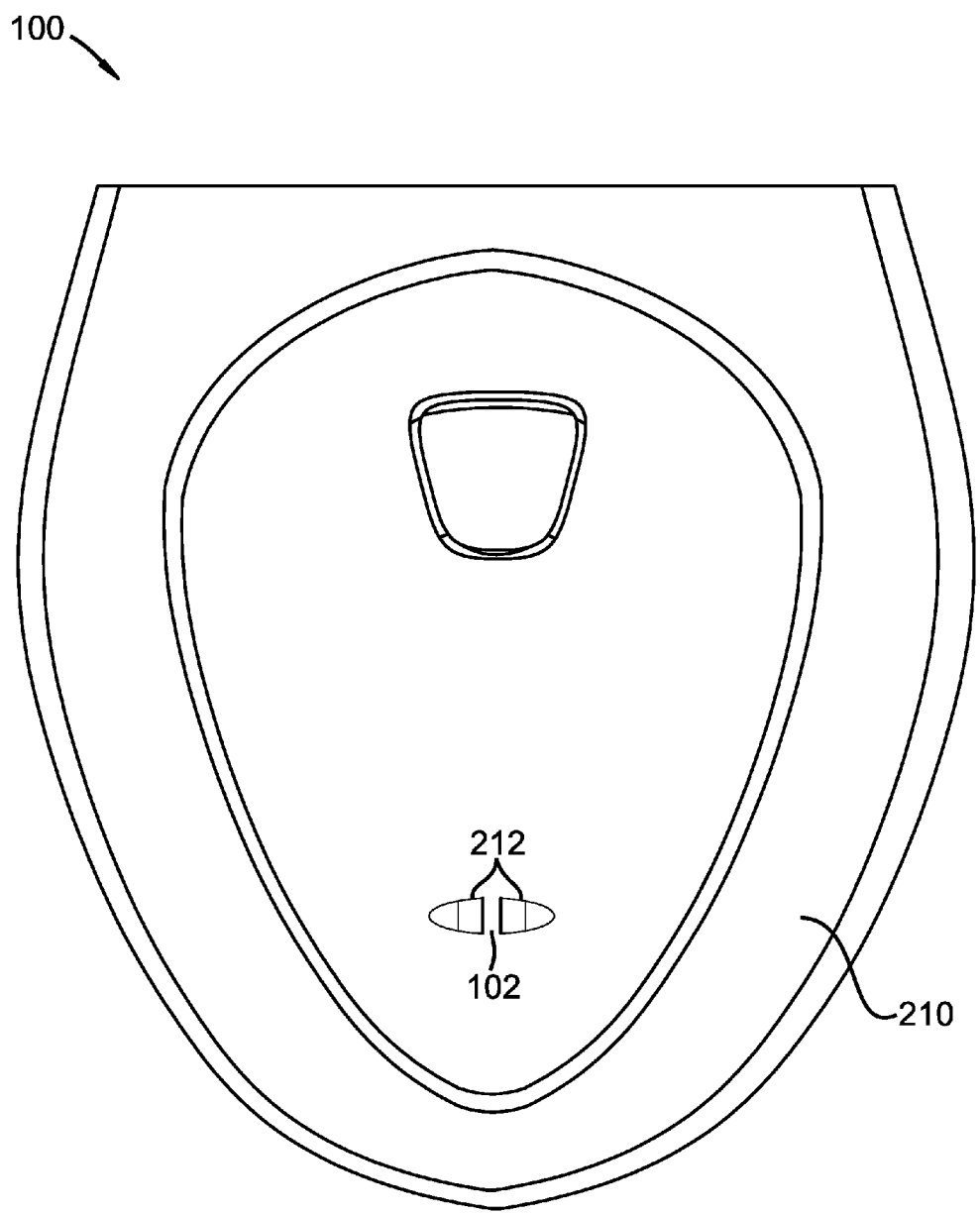
FIG. 2A is an overhead view of a toilet, according to one embodiment, with a urine-specimen-capture slit.

FIG. 2A is an overhead view of a toilet 100, according to one embodiment, with a urine-specimen-capture slit 102. The toilet 100 may comprise a seat 210 that rests upon the toilet-bowl rim (see FIG. 1). A flange 212 within the toilet bowl 104 may form the contours of the urine-specimen-capture slit 102.

Figure 2B:
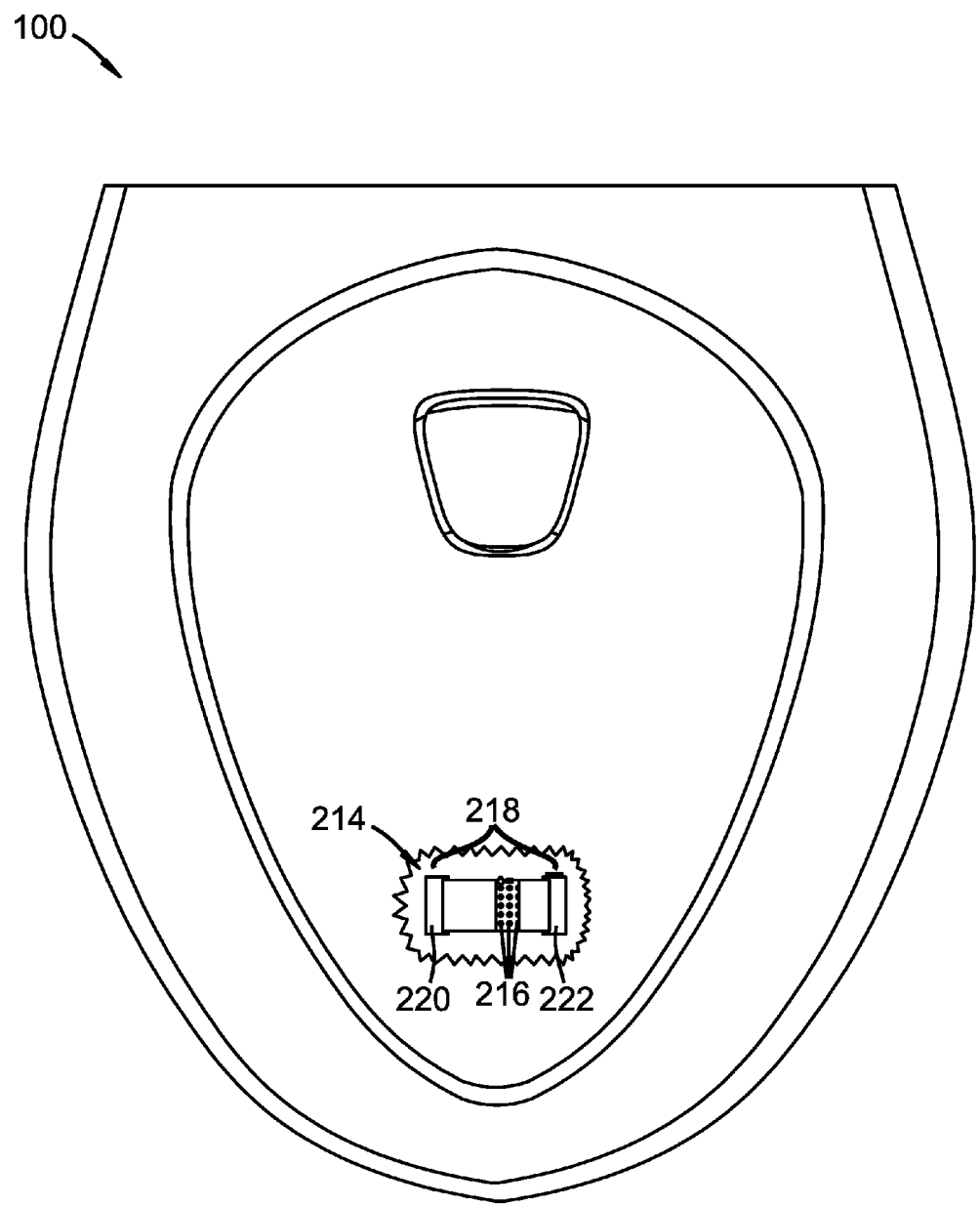
FIG. 2B is an overhead view of the toilet of FIG. 2A, in which the urine-specimen-capture slit is cut out to expose a urinalysis cassette.

FIG. 2B is an overhead view of the toilet 100 of FIG. 2A, in which the urine-specimen-capture slit (see FIG. 2A) is cut out to expose a urinalysis cassette 214. The urinalysis cassette 214 may include a multitude of absorbent-material segments 216 positioned on the surface of a roll of contiguous strips 218. The urinalysis cassette 214 may also house a first spool 220 and a second spool 222.

Figure 3A:
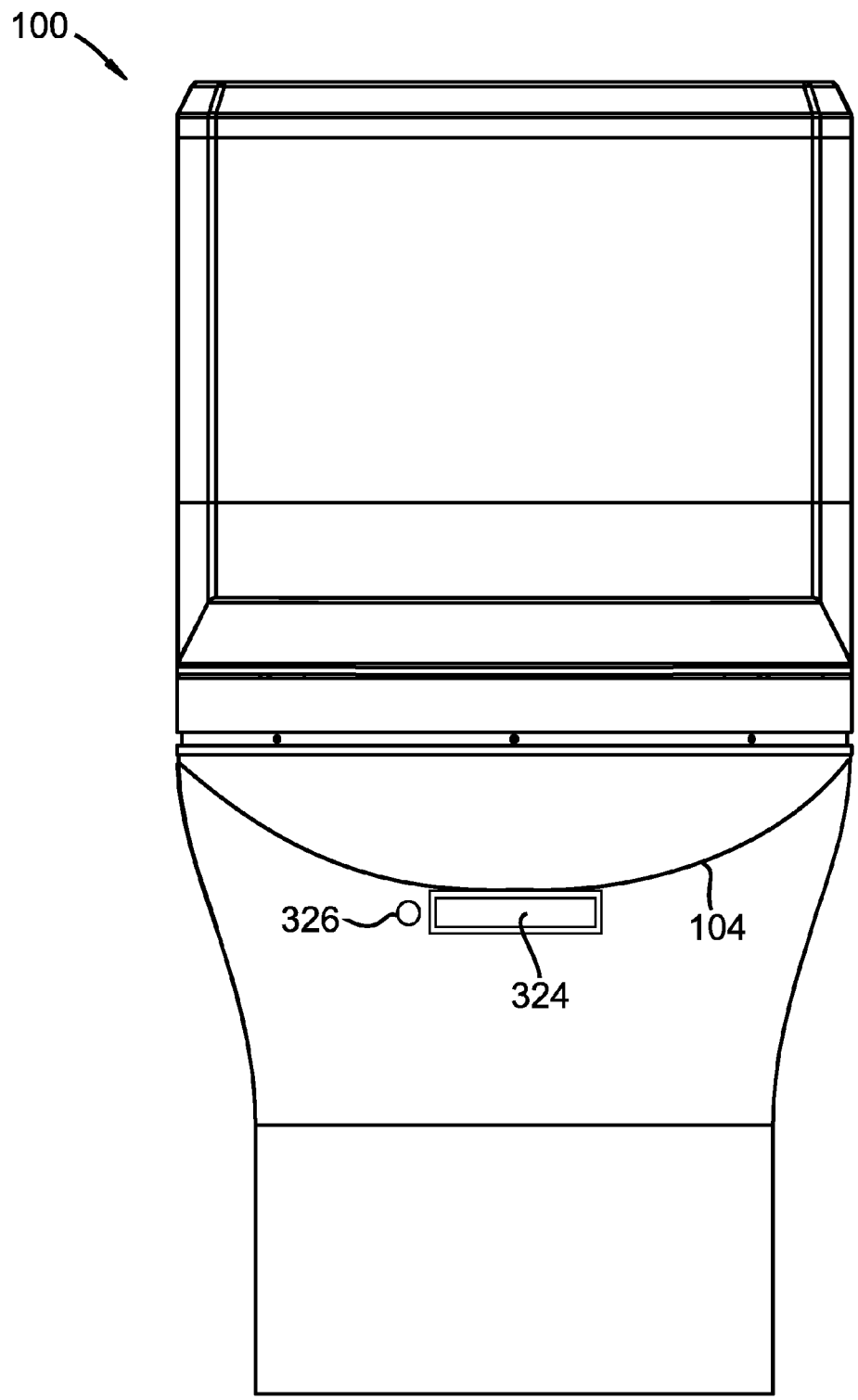
FIG. 3A is a frontal view of a toilet, according to one embodiment, with a flap to access the urinalysis cassette.

FIG. 3A is a frontal view of a toilet 100, according to one embodiment, with a flap 324 to access the urinalysis cassette (see FIG. 2B). The flap 324 may be opened with a button 326, or may open from the insertion from the urinalysis cassette (see FIG. 2B) itself. The flap 324 may be positioned below the curvature of the toilet bowl 104.

Figure 3B:
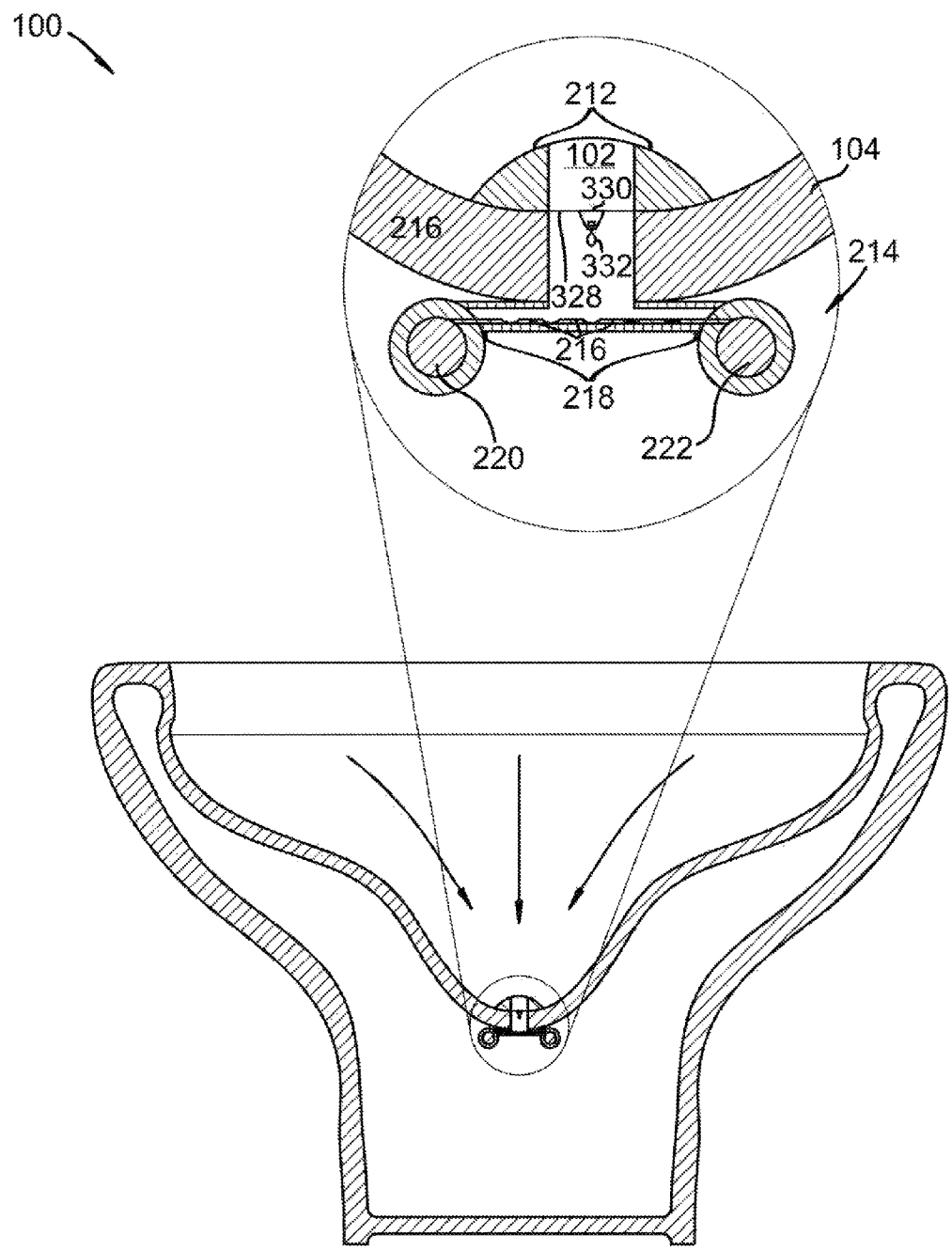
FIG. 3B is a frontal-cross-sectional view of one embodiment of the toilet of FIG. 3A, with a magnified view of a urinalysis cassette.

FIG. 3B is a frontal-cross-sectional view of one embodiment of the toilet 100 of FIG. 3A, with a magnified view of a urinalysis cassette 214. The toilet 100 may include a housing 328 attached to a nozzle 330, from which a urine specimen 332 may be dispensed. The housing 328 may be positioned between a flange 212 and the toilet bowl 104, and within the urine-specimen-capture slit 102. The urinalysis cassette 214 may include a first spool 220 and a second spool 222, which may rotate and move a roll of contiguous strips 218. The roll of contiguous strips 218 may include a plurality of absorbent-material segments 216 on the surface.

Figure 4A:
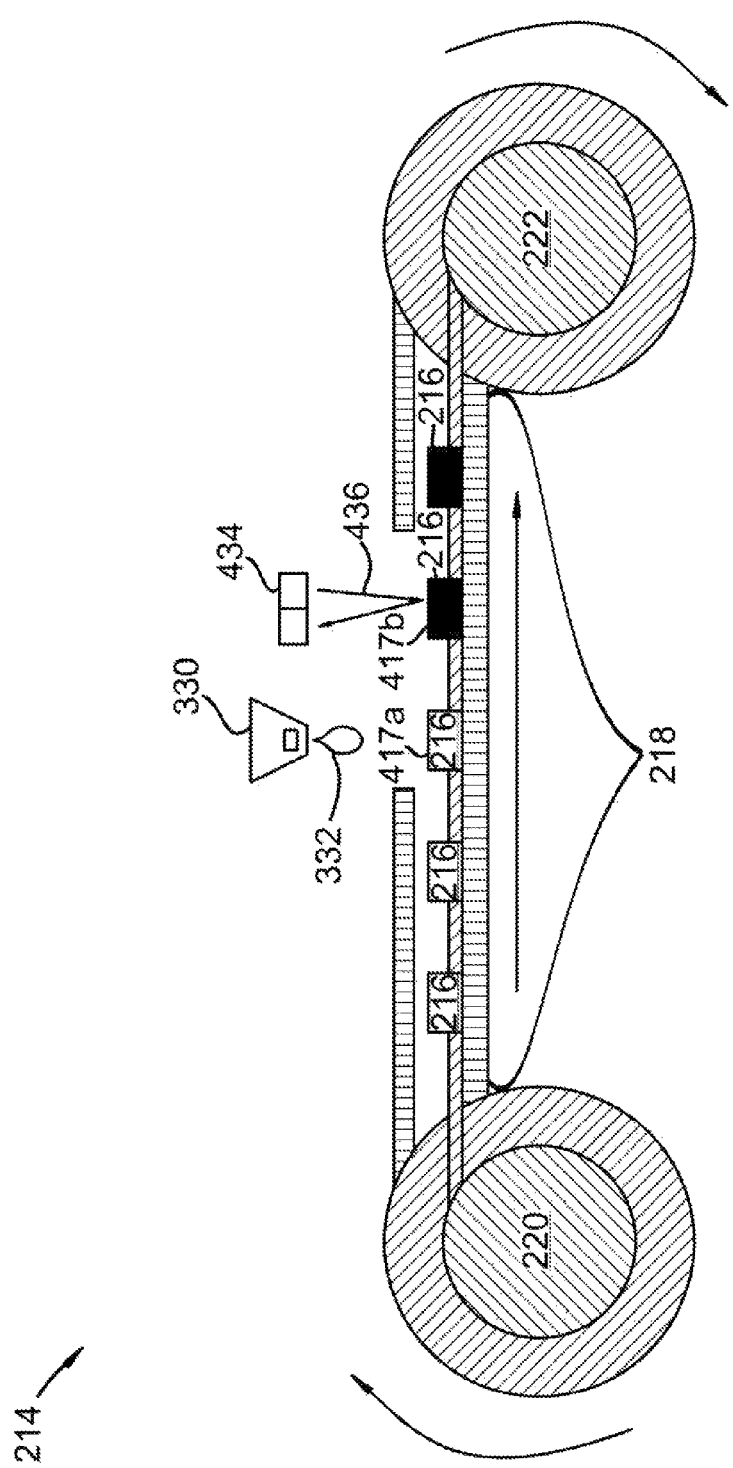
FIG. 4A is a cross-sectional view of a urinalysis cassette, according to one embodiment, in which a plurality of absorbent-material segments take the form of protuberances on the surface of the roll of contiguous strips.

FIG. 4A is a cross-sectional view of a urinalysis cassette 214, according to one embodiment, with a first spool 220 and a second spool 222. A plurality of absorbent-material segments 216 take the form of protuberances on the surface of the roll of contiguous strips 218. The nozzle 330 may dispense a urine specimen 332 onto one or more absorbent-material segments 216 comprising reagent-imbued protrusions 417A. The reagent-imbued protrusions 417A may become colored protrusions 417B, which may depend on the chemical reaction between the urine specimen 332 and the color-change reagent. A light source 434 may emit light 436 onto the colored protrusions 417B to measure reflectivity of specific color wavelengths.

Figure 4B:
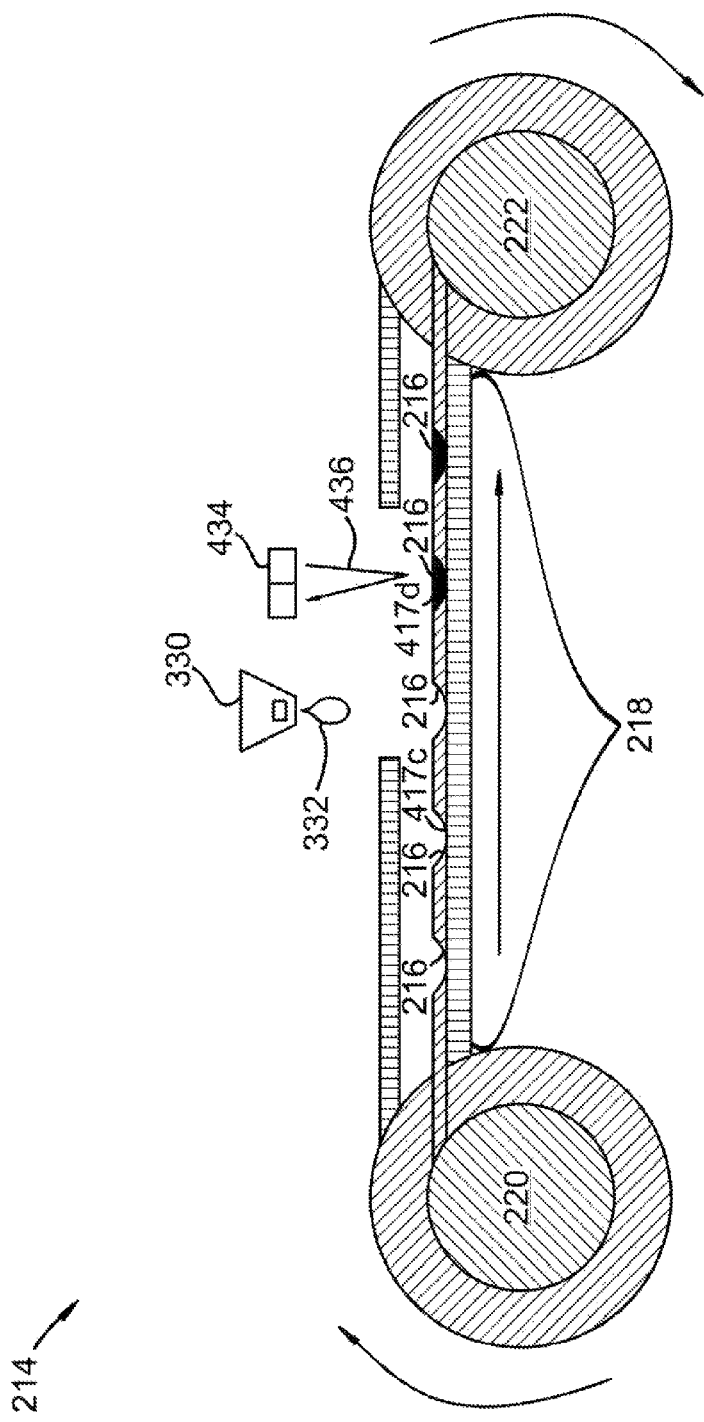
FIG. 4B is a cross-sectional view of the urinalysis cassette of FIG. 4A, with absorbent-material segments in the form of dimples in the roll of contiguous strips.

FIG. 4B is a cross-sectional view of the urinalysis cassette 214 of FIG. 4A, with absorbent-material segments 216 in the form of dimples in the roll of contiguous strips 218. The nozzle 330 may dispense a urine specimen 332 onto one or more absorbent-material segments 216 comprising reagent-imbued dimples 417C. The reagent-imbued dimples 417C may become colored protrusions 417D based on the chemical reaction between the urine specimen 332 and the color-change reagent. A light source 434 may emit light 436 onto the colored protrusions 417D to measure the reflectivity of specific color wavelengths.

Figure 5A:
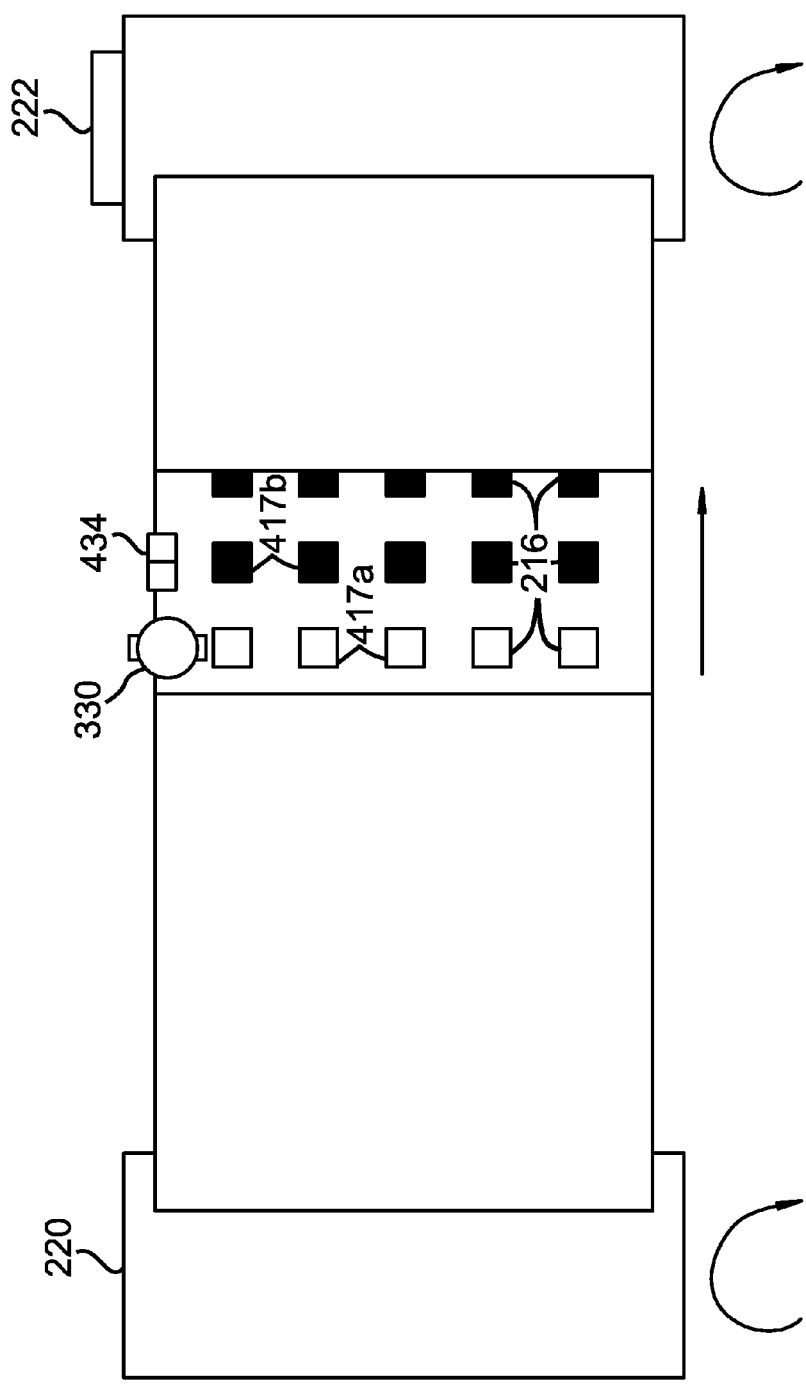
FIG. 5A is an overhead view of one embodiment of a urinalysis cassette, in which absorbent-material segments take the form of protuberances on the surface of the roll of contiguous strips.

FIG. 5A is an overhead view of one embodiment of a urinalysis cassette 214, in which absorbent-material segments 216 take the form of protuberances on the surface of the roll of contiguous strips 218. The urinalysis cassette 214 may include a first spool 220 and a second spool 222, with a nozzle 330 in between. The absorbent-material segments 216 leave the first spool 220 as reagent-imbued protrusions 417A, but become colored protrusions 417B after the nozzle 330 dispenses urine upon the reagent-imbued protrusions 417A. A light source 434 may be used to measure the reflectivity of specific color wavelengths from the colored protrusions 417B.

Figure 5B:
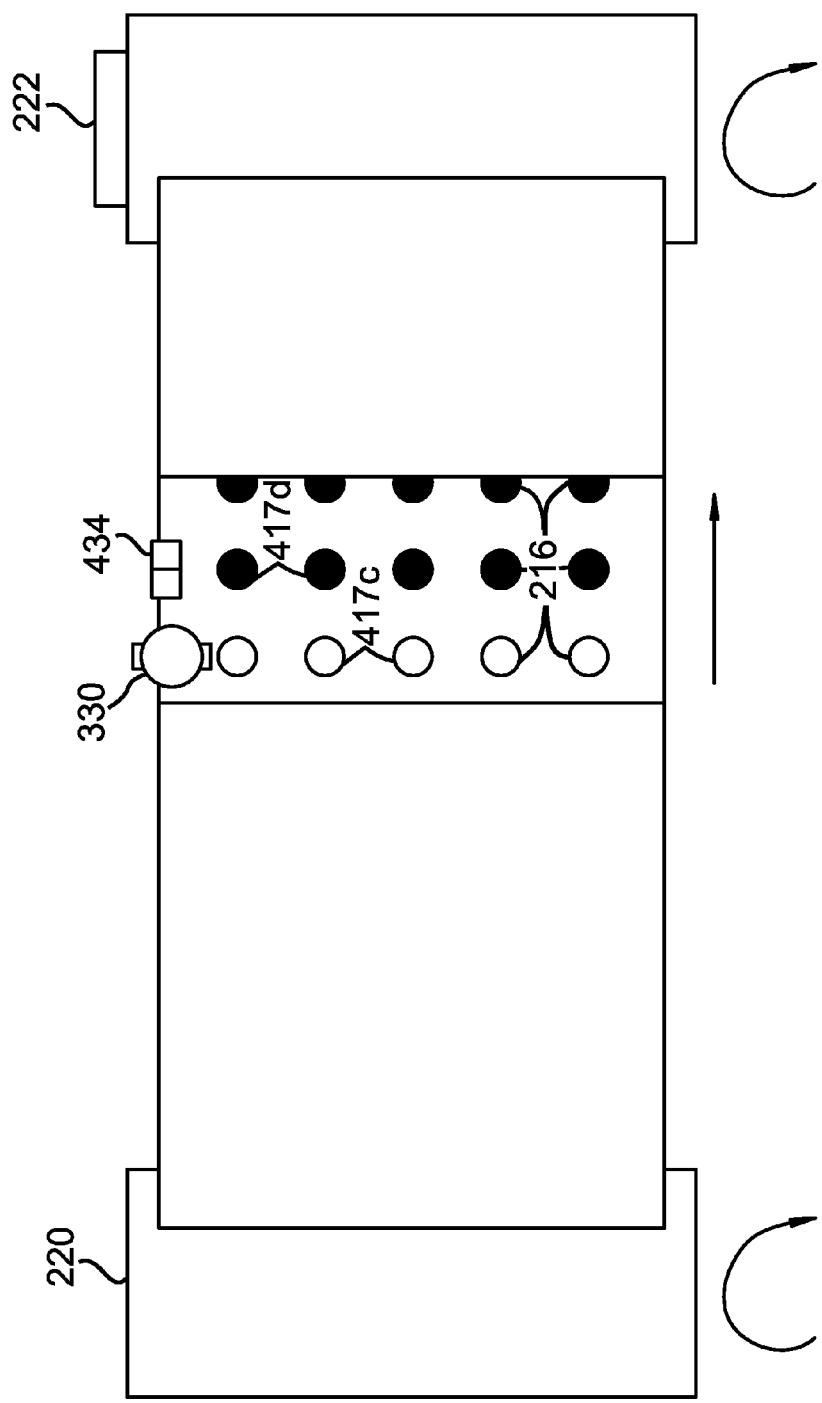
FIG. 5B is an overhead view of the urinalysis cassette of FIG. 5A, in which absorbent-material segments take the form of dimples on the roll of contiguous strips.

FIG. 5B is an overhead view of the urinalysis cassette 214 of FIG. 5A, in which absorbent-material segments 216 take the form of dimples on the roll of contiguous strips 218. The urinalysis cassette 214 may include a first spool 220 and a second spool 222, with a nozzle 330 in between. The absorbent-material segments 216 leave the first spool 220 as reagent-imbued dimples 417C, but become colored dimples 417D after the nozzle 330 dispenses urine upon the reagent-imbued dimples 417C. A light source 434 may be used to measure the reflectivity of specific color wavelengths from the colored dimples 417D.

Figure 6:
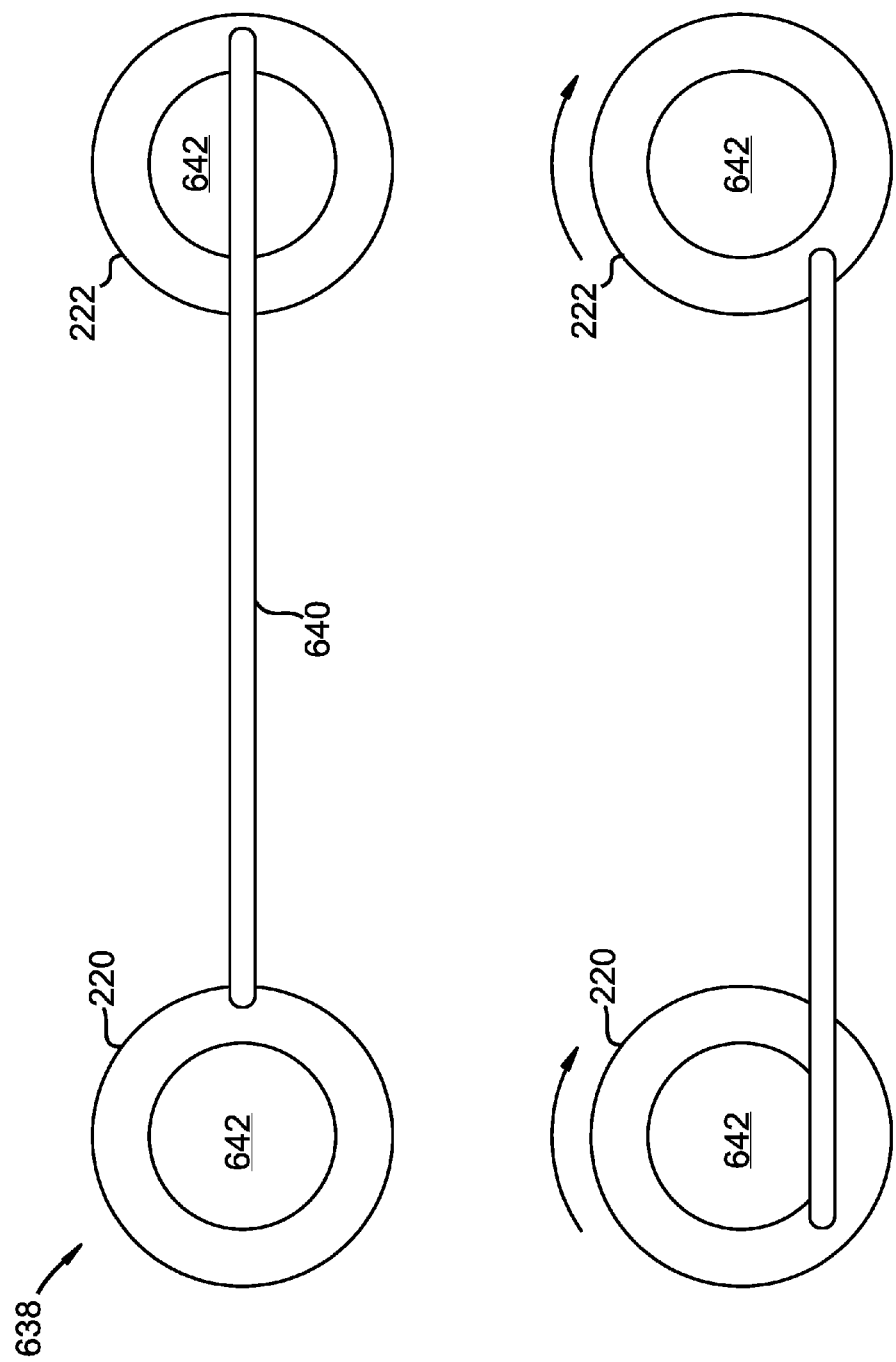
FIG. 6 is a perspective view of one embodiment of a rotation mechanism for rotational coordination of a first spool and second spool.

FIG. 6 is a perspective view of one embodiment of a rotation mechanism 638 for rotational coordination of a first spool 220 and second spool 222. In one embodiment, the rotation mechanism 638 may include a connecting rod 640 may connect the first spool 220 to the second spool 222, such that movement of one spool around an axis 642 consequently turns the other spool.

Figure 7:
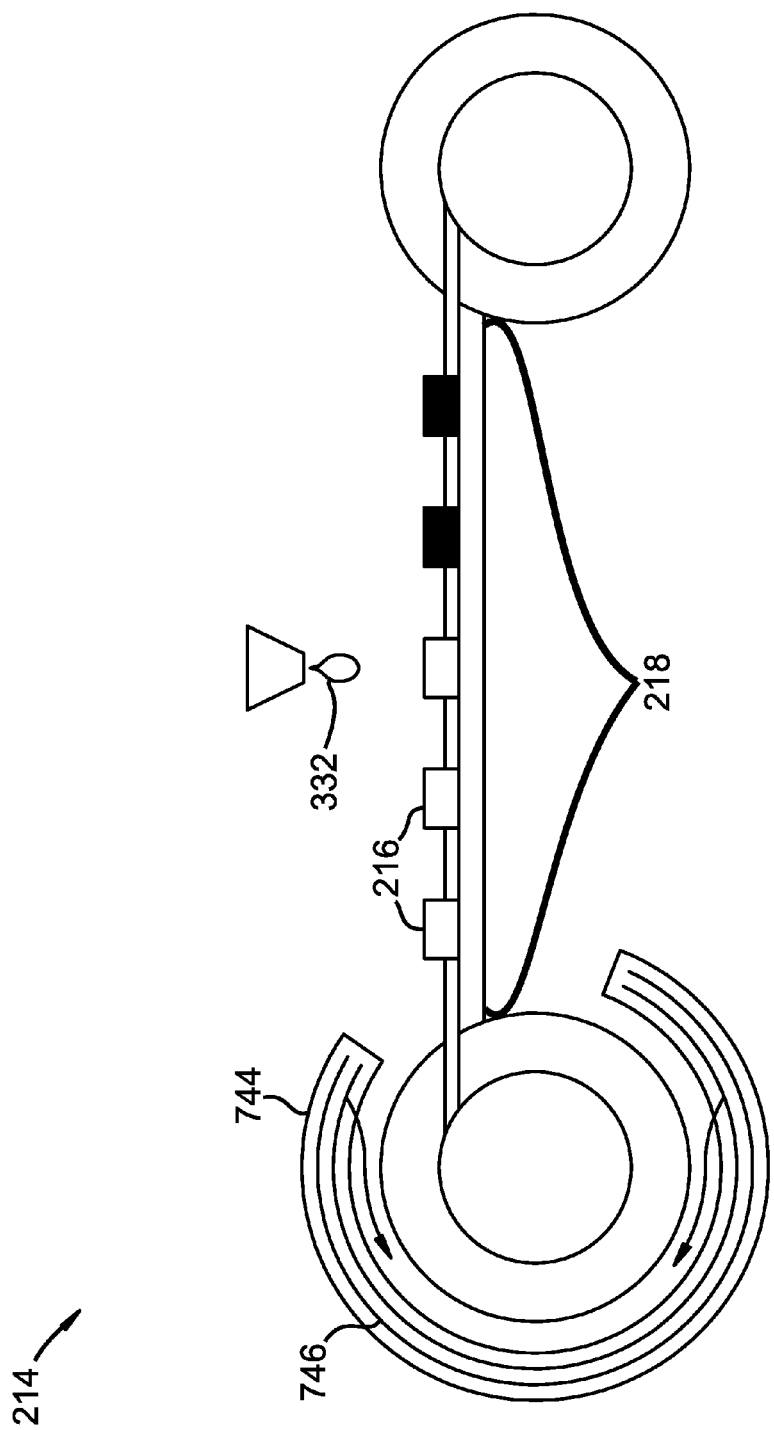
FIG. 7 is a cross-sectional view of a urinalysis cassette comprising a reagent-temperature-control system, according to one embodiment.

FIG. 7 is a cross-sectional view of a urinalysis cassette 214 comprising a reagent-temperature-control system 744, according to one embodiment. The reagent-temperature-control system 744 may release hot or cold air from one or more vents 746. The roll of contiguous strips 218 may be incubated at a specified temperature such that the color-change reagent on the absorbent-material segments 216 may interact with the urine specimen 332 under controlled conditions.

Figure 8:
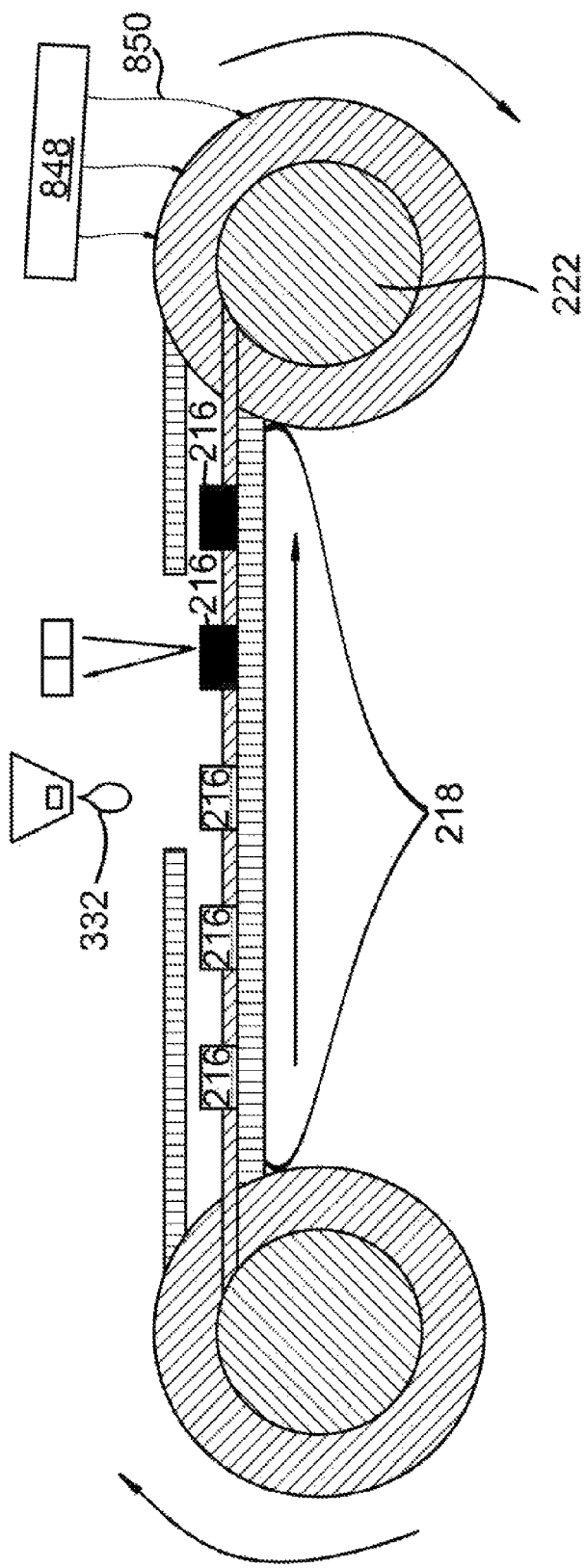
FIG. 8 is a perspective view of one embodiment of a urinalysis cassette comprising a heat source to apply heat to moist, absorbent-material segments and/or wet portions of a roll of contiguous strips.

FIG. 8 is a perspective view of one embodiment of a urinalysis cassette 214 comprising a heat source 848 to apply heat 850 to moist absorbent-material segments 216 and/or wet portions of a roll of contiguous strips 218. The heat 850 from the heat source 848 may be used to dry the portion of the roll of contiguous strips 218 that was exposed to a urine specimen 332 and winds around the second spool 222.

Figure 9:
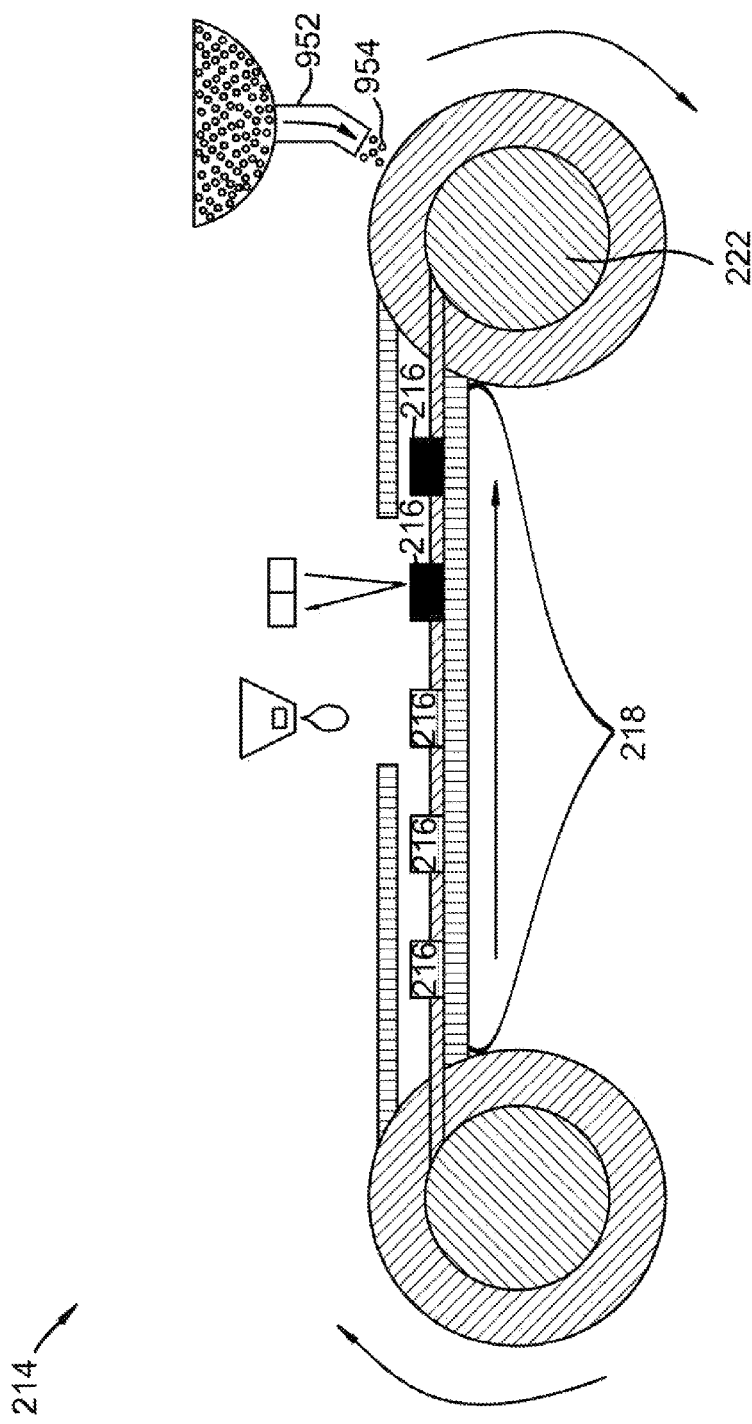
FIG. 9 is a perspective view, according to one embodiment, of a urinalysis cassette with a desiccant dispenser.

FIG. 9 is a perspective view, according to one embodiment, of a urinalysis cassette 214 with a desiccant dispenser 952. The desiccant dispenser 952 may release a desiccant 954 onto the second spool 222 of the urinalysis cassette 214. The desiccant 954 may dry the moist absorbent-material segments 216 and/or wet portions of the roll of contiguous strips 218.

Figure 10:
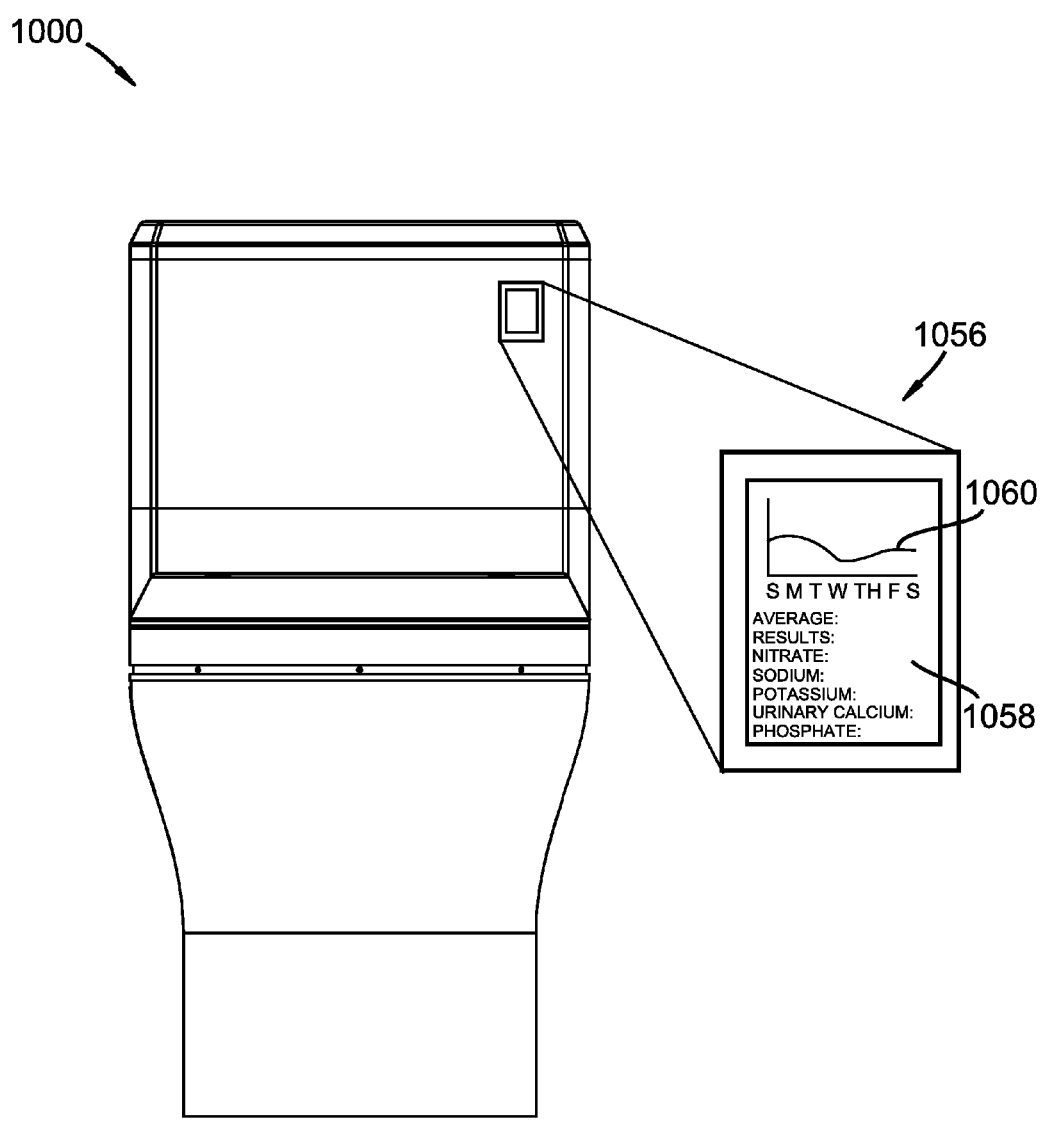
FIG. 10 is a perspective view of one embodiment of a toilet with a user interface, in which a screen provides a digital readout of urinalysis results.

FIG. 10 is a perspective view of one embodiment of a toilet 100 with a user interface 1056, in which a screen 1058 provides a digital readout 1060 of urinalysis results. The user interface 1056 may, according to one embodiment, be attached to the toilet 100. The screen 1058 of the user interface 1056 may show any number of tests and/or results that may be detected via urinalysis. The digital readout 1060 may include and/or show comparisons to previous tests, and/or baseline levels.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

It will be apparent to those having skill in the art that changes may be made to the details of the above-described embodiments without departing from the underlying principles of the invention. Embodiments of the invention in which an exclusive property or privilege is claimed are defined as follows.

The invention claimed is:
1. A toilet, comprising:
   a urinalysis cassette, wherein a roll of contiguous strips subject to one or more color-change reagents is rolled onto a plurality of spools;
   a first spool for distributing a pre-wound roll of contiguous strips;

a second spool for receiving and storing strips distributed from the first spool;

a light emitter, wherein light projects onto the strips;

a light-wavelength sensor, wherein colors on the strips are detectable;

a sensor, optical signal, and/or indicator to detect when the roll of contiguous strips are entirely transferred from the first spool to the second spool;

a urine-specimen-capture slit disposed within the toilet bowl;

a nozzle, wherein the nozzle is disposed within the urine-specimen capture slit;

a housing compartment for the urinalysis cassette located below a toilet bowl, the housing compartment comprising an orifice for receiving a urine sample, wherein the orifice is adjacent to the nozzle, wherein the nozzle is in fluid connection with the urine specimen-capture-slit and the orifice; and a wireless communications network for transmitting urinalysis results as a digital readout.

2. The toilet of claim 1, wherein the roll of contiguous strips is comprised of one or more absorbent-material segments on a surface of the contiguous strips.

3. The toilet of claim 1, wherein the roll of contiguous strips comprises an exposed strip segment that traverses a gap situated between the first spool and the second spool.

4. The toilet of claim 3, wherein the urinalysis cassette comprises a mechanism by which the first and second spools synchronously rotate a previously-specified set of degrees such that once the urinalysis of the exposed strip segment is complete, a new segment of the roll of contiguous strips traverses the gap situated between the first spool and the second spool.

5. The toilet of claim 1, further comprising an electrical power source.

6. The toilet of claim 1, further comprising one or more light sources such as light-emitting diodes, photodiodes, and/or cameras, which comprise a broadband source, a tunable narrowband filter, and/or several narrowband emitters.

7. The toilet of claim 1, further comprising a temperature control system for controlling ambient temperature near the roll of contiguous strips during chemical reactions.

8. The toilet of claim 1, further comprising a heat source to locally heat a portion of the roll of contiguous strips that is received onto the second spool such that a strip segment previously exposed to urine evaporates any moisture retained in the strip segment.

9. The toilet of claim 1, further comprising a desiccant, which is applied to a strip segment previously exposed to urine such that a portion of the roll of contiguous strips that is received onto the second spool is dried.

10. The toilet of claim 1, wherein the urinalysis cassette comprises a sanitation and/or purification system for sanitizing segments of the roll of contiguous strips that were exposed to urine.

11. The toilet of claim 1, further comprising a mechanism to produce a digital readout of a chemical reaction produced between urine and one or more color-change reagents.

12. The toilet of claim 1, further comprising computer storage memory wherein the digital readouts are stored.

13. The toilet of claim 1, further comprising a user interface, wherein urinalysis results and/or comparisons are conveyed via a visual signal and/or representation.

14. The toilet of claim 1, wherein the urinalysis cassette is removable such that the cassette is inserted into and/or accessed from the housing compartment located below the toilet bowl.

15. The toilet of claim 1, further comprising one or more nozzles located between the toilet bowl and the roll of contiguous strips such that urine passes through the one or more nozzles before coming into contact with the roll of contiguous strips.

16. The toilet of claim 15, wherein the one or more nozzles further comprises piezoelectric inkjet pumps, or similar nonthermal microdispensers for dispensing color-change reagent.

17. The toilet of claim 1, further comprising a housing wherein one or more movable and/or rotatable nozzles are attached.

18. The toilet of claim 1, comprising a motor that rotates the first spool and/or second spool such that a portion of the roll of contiguous strips is dispensed from the first spool and received by the second spool.

19. The toilet of claim 1, wherein the wireless communications network further comprises a signal produced by the digital readout to activate the motor and/or move the first spool and/or second spool in preparation for a future urinary event.

* * * * *